US010806645B2

(12) United States Patent
Shahir

(10) Patent No.: US 10,806,645 B2
(45) Date of Patent: Oct. 20, 2020

(54) WOUND CARE PRODUCT AND A METHOD OF USING A WOUND CARE PRODUCT

(71) Applicant: MÖLNLYCKE HEALTH CARE AB, Gothenburg (SE)

(72) Inventor: Michael Shahir, Askim (SE)

(73) Assignee: Mölnlycke Health Care AB, Gothenburg (SE)

(*) Notice: Subject to any disclaimer, the term of this patent is extended or adjusted under 35 U.S.C. 154(b) by 409 days.

(21) Appl. No.: 15/113,454

(22) PCT Filed: Dec. 9, 2014

(86) PCT No.: PCT/EP2014/077083
§ 371 (c)(1),
(2) Date: Jul. 22, 2016

(87) PCT Pub. No.: WO2015/113683
PCT Pub. Date: Aug. 6, 2015

(65) Prior Publication Data
US 2016/0374873 A1    Dec. 29, 2016

(30) Foreign Application Priority Data
Jan. 28, 2014   (EP) .................................... 14152897

(51) Int. Cl.
*A61F 15/00*    (2006.01)
*A61F 13/00*    (2006.01)
*A61F 13/551*   (2006.01)

(52) U.S. Cl.
CPC ...... *A61F 15/001* (2013.01); *A61F 13/00042* (2013.01); *A61F 13/00072* (2013.01);
(Continued)

(58) Field of Classification Search
CPC .......... A61F 17/00; A61F 15/00; A61F 13/00; A61F 13/00072; A61F 13/00076;
(Continued)

(56) References Cited

U.S. PATENT DOCUMENTS 4,170,300 A * 10/1979 Pick ...................... A61B 50/33
                                                         206/365
4,903,837 A *  2/1990 Duello .................. A61F 15/001
                                                         206/233
(Continued)

FOREIGN PATENT DOCUMENTS

EP          0650713 A2    5/1995

OTHER PUBLICATIONS

International Search Report dated Mar. 13, 2015 for application PCT/EP2014/077083, filed on Dec. 9, 2014 and published as WO 2015/113683 dated Aug. 6, 2015 (Applicant—Molnlycke Health Care AB // Inventor—Shahir) (3 pages).
(Continued)

*Primary Examiner* — Steven A. Reynolds
*Assistant Examiner* — Javier A Pagan
(74) *Attorney, Agent, or Firm* — Ballard Spahr LLP

(57) ABSTRACT

The invention relates to a wound care product, comprising a wound care article located in a sterilized sealed chamber defining a sterile environment. The wound care product also comprises an openable and reclosable container which has at least one outer surface portion in said sterile environment. The invention further relates to a method for using such a wound care product.

17 Claims, 7 Drawing Sheets

(52) U.S. Cl.
CPC ...... *A61F 13/00076* (2013.01); *A61F 13/551* (2013.01); *A61F 2013/00897* (2013.01); *A61F 2013/55195* (2013.01)

(58) Field of Classification Search
CPC ............ A61F 13/0008; A61F 13/00089; A61F 13/551; A61F 2013/55125; A61F 2013/55155; A61F 2013/8462
See application file for complete search history.

(56) References Cited

U.S. PATENT DOCUMENTS

| | | | |
|---|---|---|---|
| 6,140,549 A | 10/2000 | Pompei, Jr. | |
| 7,578,391 B2 * | 8/2009 | Nakamura | A61B 50/30 206/223 |
| 2007/0049891 A1 | 3/2007 | Clark et al. | |

OTHER PUBLICATIONS

Written Opinion dated Mar. 13, 2015 for application PCT/EP2014/077083, filed on Dec. 9, 2014 and published as WO 2015/113683 dated Aug. 6, 2015 (Applicant—Molnlycke Health Care AB // Inventor—Shahir) (5 pages).

\* cited by examiner

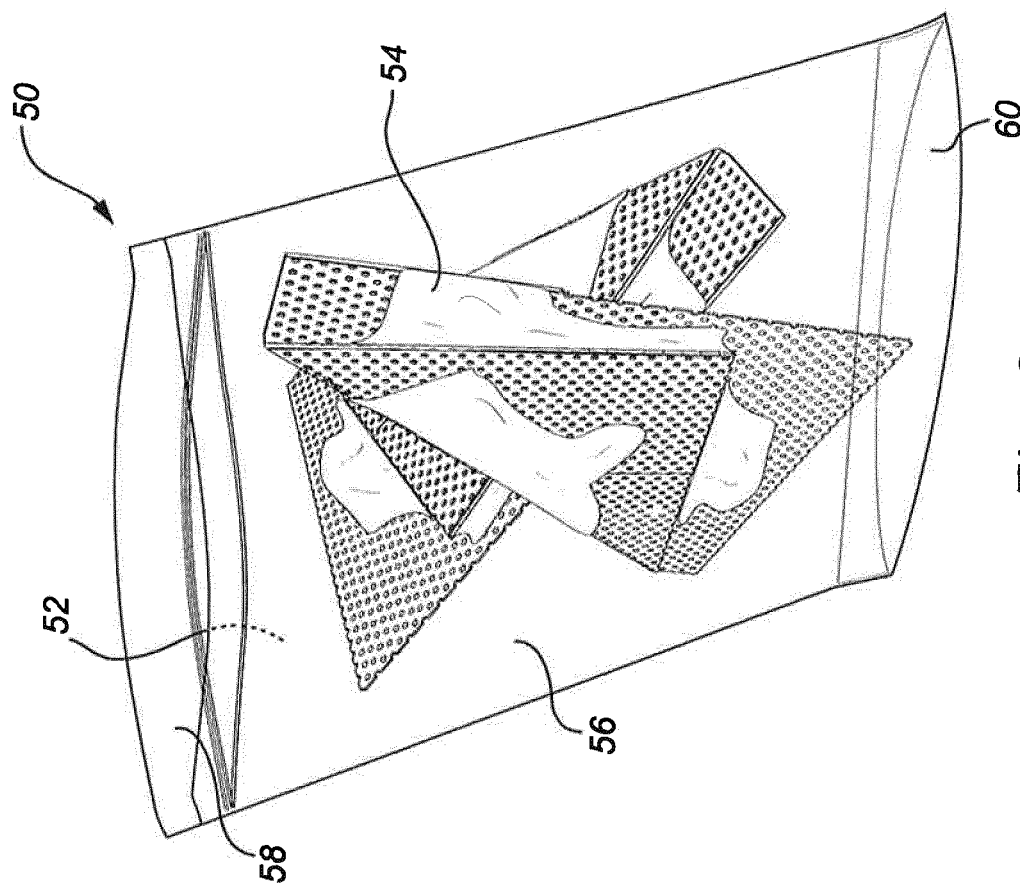
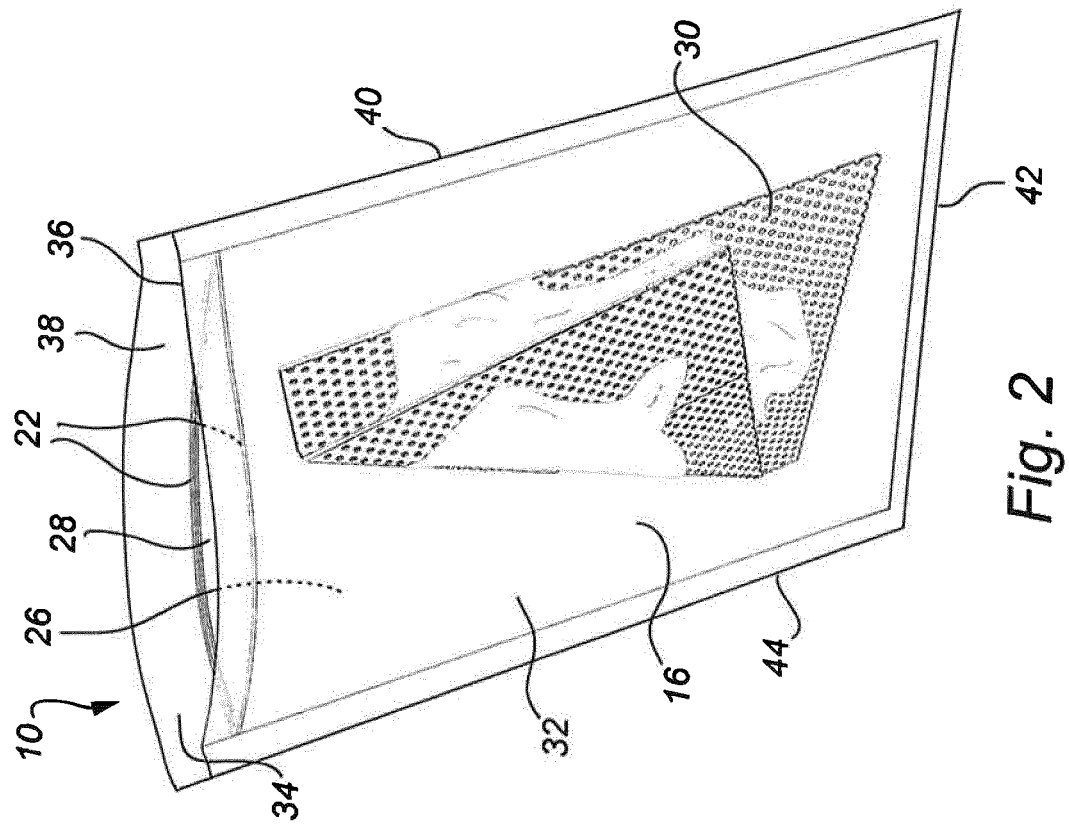

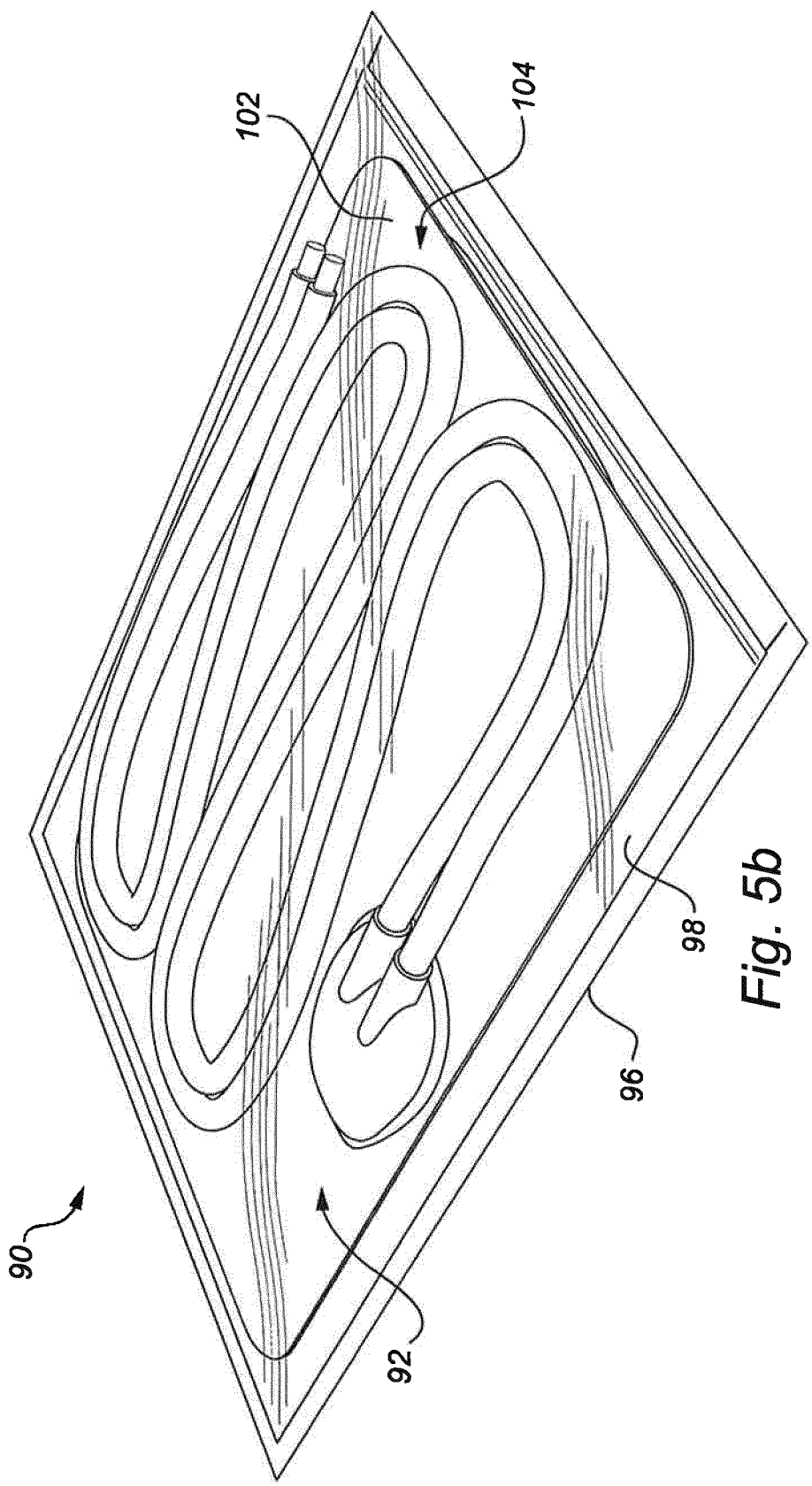

WOUND CARE PRODUCT AND A METHOD OF USING A WOUND CARE PRODUCT

CROSS-REFERENCE TO RELATED APPLICATIONS

This application is a U.S. National Phase Application of International Application No. PCT/EP2014/077083, filed Dec. 9, 2014, which claims priority to European Patent Application No. 14152897.6, filed Jan. 28, 2014, each of which are hereby incorporated by reference in their entirety.

TECHNICAL FIELD

The present invention relates to a wound care product comprising at least one sterilized wound care article. The present invention also relates to a method of using a wound care product which comprises a sterilized wound care article.

BACKGROUND ART

Sterilized wound care articles, such as absorbent pads, wound dressings, wound fillers, swabs, wipes and wound diagnostic devices, are commonly used for treating wounds, in particular in hospitals and in other nursing facilities. When replacing a used wound care article with a fresh one, the used wound care article is removed and thrown away, for instance, into a waste bin. The fresh wound care article can then be applied onto the patient.

The used wound care article may sometimes present an unpleasant odor. Furthermore, it may carry infectious residues from the wound, thus presenting a health hazard even after having been thrown in the waste bin.

SUMMARY OF THE INVENTION

An object of the present invention is to alleviate the drawbacks mentioned above. This and other objects, which will become apparent in the following, are accomplished by a wound care product and a method of using a wound care product as defined in the accompanying independent claims.

The present invention is based on the insight that a container, such as a disposable waste bag, can be used with double protecting functions, the first one being for protecting an unused sterilized wound care article and the second one being for protecting people/environment from being contaminated by a used wound care article. In particular, it has been realized that the container, in its unused state may form a protecting component for the likewise unused sterilized article. Such a protecting component may, for instance, be part of a protecting packaging for the wound care article. Another possibility is that it may be or form part of one or more protecting layers, either as loose layer(s) or attached layers such as a release layer attached to, for instance, an adhesive layer with which the sterilized unused wound care article is coated.

Thus, according to a first aspect of the inventive concept, a wound care product is provided. The wound care product comprises:
- a sterilized sealed chamber defining a sterile environment,
- at least one sterilized wound care article contained in the sterilized sealed chamber,
- a container having inner surface portions defining an interior container space and outer surface portions facing away from said interior container space, the container being openable for enabling access to said interior container space and reclosable for closing said interior container space, wherein at least one of said outer surface portions is in said sterile environment.

Since the container is openable, it can be used to receive a used wound care article. Furthermore, since it is reclosable, it may be closed after the used wound care article and/or other waste material left over after applying the wound care article, such as release liners, has/have been put into the container. Thus, interior container space has a protecting function of avoiding, or at least reducing, contaminants from being spread from the used wound care article.

It should be understood that the container is not only suitable for receiving used articles. It may in some embodiments be used for receiving non-used material. For instance, in some example embodiments the opened container may be used for receiving release liners, unused bits of wound care articles such as dressings and/or fillers (e.g. foams, gauzes etc.), packaging materials that are not part of the container, swabs and/or wound diagnostic devices. In, for example, negative pressure wound therapy (NPWT) the medical personnel may start off from a large piece of foam and remove scraps of material to obtain a size of the foam which is suitable for the wound. Such scraps of foam or other filler material that has not been applied to the patient, may suitably be put in the opened container.

However, before using it for receiving a used (or non-used) wound care article, and possibly other waste as well, the wound care article protects an unused sterilized wound care article. In particular, the exterior of the container, or at least an outer surface portion thereof, may be arranged to provide such a protecting function.

As will be exemplified in more detail below, the container may form part of a package for a wound care article. For instance, the container may be a first packaging portion which is attached to a second packaging portion, such as a base layer, wherein a wound care article is held between the first and second packaging portions in a sealed and sterilized environment. Thus, although one outer surface portion of the container may face away from the sealed sterilized environment and thus be non-sterile, an oppositely facing outer surface portion will form a wall defining the chamber having the sterile environment.

As will also be exemplified, in other embodiments the entire container may be inside the sterile environment. The container may have a cushioning effect, reducing the risk of the wound care article being exposed to inadvertent damaging, and/or it may be attached to and protect an adhesive coating of the wound care article.

The sterilized sealed chamber may be considered as being formed by a package, the inside of which defines a sterile environment. According to at least one exemplary embodiment, said sterilized sealed chamber is at least partly defined by a layer which does not form part of the container, i.e. a layer which is a different entity than the actual container. In some exemplary embodiments, said layer which does not form part of the container may (for instance along peripheral portions thereof) be attached to one side of the container. Said one side of the container and the attached layer may thus define, or at least partly define, the sterilized sealed chamber.

In at least some exemplary embodiments, the sterilized sealed chamber may be defined by two layers which do not form part of the container. For instance, as already mentioned, the entire container may be contained inside the sterile environment.

As mentioned above, the sterilized sealed chamber may be considered as being formed by a package, the inside of which defines a sterile environment. To obtain such a sterilized sealed chamber, a portion of the package may suitably be permeable to a sterilant, such as a sterilizing gas. This has been considered in at least one exemplary embodiment, wherein said sterilized sealed chamber is at least partly defined by a gas permeable front layer.

According to at least one exemplary embodiment, said sterilized sealed chamber is at least partly defined by said container, said container being releasably attached to said front layer. Thus, the container has the function of forming a chamber defining wall portion, i.e. a part of a packaging for an unused article, and then the function of receiving a used article and other waste for disposal.

It may be practical to use as a permeable front layer any standard piece of packaging material that is permeable to a sterilant. However, in at least some embodiments, it would be conceivable to instead (or also) make the container, or at least portions of the container, of a material permeable to a sterilant, thereby enabling sterilization of the enclosed chamber containing the unused wound care article in order to create a sterile environment.

According to at least one exemplary embodiment, one of the outer surface portions of the container faces said front layer and is at its periphery or near its periphery sealed to said front layer. Thus, the sealing provides a boundary for the sterilized environment for the sterilized and unused wound care article. Although in some embodiments said outer surface portion of the container is along its entire periphery sealed to the front layer, in other embodiments said outer surface is only sealed to the front layer along part of the periphery. For instance, said outer surface of the container may have portions extending past the sealing interface with the front layer. Such extending portions may be for providing a grip or for providing expandable parts of the container, for instance by presenting a bellows portion beyond the seal, or for other suitable purposes.

Said outer surface of the container facing and being sealed to the front layer may be regarded as a back layer. However, in some embodiments, a separate back layer may be attached and sealed to the front layer. In such embodiments of the wound care product, the container could be located between the front layer and the back layer, suitably next to the unused wound care article. The provision of a back layer is reflected in at least one exemplary embodiment in which the sterilized sealed chamber is at least partly defined by a back layer, said back layer being releasably attached to said front layer.

As mentioned previously, in some of the embodiments in which the entire container is located inside the sterilized sealed chamber, it could function as a release layer which is attached to an adhesive layer of the wound care article. However, it should be noted that in other embodiments, the container could, as described above, have an outer surface facing and being sealed to the front layer to define said sterilized sealed chamber. In this latter case, a wound care article having an adhesive layer could have a separate release layer as is customary for such kind of wound care articles, but in at least some of these embodiments, the outer surface of the container facing the front layer and defining the sterilized sealed chamber may also function as a release layer which is attached to an adhesive layer of the unused sterilized wound care article. In other words, according to at least some exemplary embodiments, the container is releasably attached to at least one of said front layers and said sterilized wound care article.

From the above, it should also be understood that, in general terms and for at least some embodiments (regardless of whether the container is located inside the sealed chamber or is defining the sealed chamber), said container is releasably attached to said at least one sterilized wound care article.

Furthermore, according to at least one exemplary embodiment, said sterilized wound care article comprises a wound contact layer provided with an adhesive coating, wherein one of the outer surface portions of the container forms a release layer releasably attached to the adhesive coating on the wound contact layer. The adhesive coating is suitably skin friendly. The wound contact layer may, for instance, be in the in the form of a relatively thick pad or a relatively thin film layer.

According to at least one exemplary embodiment, said container is in the form of a bag, such as a plastic bag or a bag comprising at least one of a plastic or paper material, such as a paper/plastic laminate. The bag may be transparent, or at least partly transparent. In some embodiments, the bag may be at least partly opaque. Although the major part of the bag is suitably formed in the same material or same combination of materials, in some embodiments, different portions of the bag may be made of different materials. For instance, in a flat condition of the bag, a first layer of the bag being closest to or in contact with the front layer may be made (at least partly) from a first material while a second layer of the bag (on the opposite side of the first layer of the bag) may be made (at least partly) from a second material which is not present in the first layer.

The presence of a first and second layer is also reflected in at least the following embodiment, according to which the container comprises a first layer and a second layer attached to said first layer to define said interior container space, wherein the second layer extends beyond an edge of the first layer to form a grippable tab. Suitably, the second layer may have an area substantially corresponding to the front layer. In such case, the peripheral edges of the front layer and the peripheral edges of the second layer may be substantially aligned. Since the second layer may extend beyond an edge of the first layer to form a grippable tab, front layer may also extend beyond said edge of the first layer. Nevertheless, the first layer of the container may still be sealed to the front layer, wherein the portion of the second layer of the container (forming the tab) and the portion of the front layer which both extend beyond said edge of the first layer, will overlap each other without being adhered to each other.

According to at least one exemplary embodiment, said first layer is sealingly and removably attached to said front layer to form said sterilized sealed chamber. Such embodiments may suitably also comprise the configurations of the second layer, in particular, the extension and conformity with the front layer as described above.

Different versions of the container may be provided with different opening/closing means. According to at least one exemplary embodiment of the wound care product said first and second layer comprises mutually cooperating zipper means for opening and closing the container. The container may be reclosed by pressing the zipper means together. In some embodiments, the zipper means may be pressed together by additional closing means, such as a slider which may be pulled along the length of the zipper means. Typically, when displacing the slider in one direction the zipper means are urged together to close the container, and when pulling the slider in the opposite direction the zipper means are separated to open the container. Although zipper means provide an easily manufactured and handled opening/closing means, others are also conceivable. For instance, in some exemplary embodiments the opening/closing means may be provided by an adhesive strip or the like which maintains substantial amount of its adhering capability after opening the container, thus also enabling reclosing in a satisfactory manner. Other conceivable embodiments may include drawstring containers.

In the case of a grippable tab being provided, for instance as exemplified above, such a grippable tab could, according to at least one exemplary embodiment, extend from the opening/closing means (for instance mutually cooperating zipper means) to an edge of said second layer of the container. Thus, the tab may be gripped to remove the container from the front layer in order to get access to the unused wound care article, without opening the container if it has originally been delivered in a closed position.

The container may in some exemplary embodiments comprise two substantially flat layers, such as a first layer and a second layer as described above, with any suitably opening/closure means. The container may be delivered flat before use, wherein the volume between the first and the second layer is very small or almost neglectable. Then when the container is opened portions of the first and second layer may be separated from each other (similarly to a plastic pocket for office binders) wherein the available volume is increased to receive items. This type of container may be suitable for receiving smaller items, such as some wound contact layers or gauze dressings and other small pieces of waste.

However, the present inventive concept may also be used in connection with larger items and/or kits that generate a lot of waste during use. For instance, foams or other wound fillers may be cut to appropriate shape and size, and the leftovers that are not used may be placed in the opened container. Of course, the used parts of the foam may subsequently also be placed in the same container or in another container. Other examples of such items are negative pressure wound therapy (NPWT) kits which may include a relatively large wound pad to be placed in the wound, a wound cover, and a conduit configured to transmit negative pressure from a negative pressure source. The wound pad, the wound cover and the conduit (which may include a cup-shaped nozzle and a single or multi-lumen tube) are wound care articles which may be sterilized and provided in the sterilized chamber of the wound care product. When the relatively bulky items are to be disposed of, a relatively large internal space in the container may be required. Such large container space is reflected in accordance with at least one exemplary embodiment, according to which the container is expandable such that in an expanded state said first layer and said second layer are, at least locally, spaced apart by one or more interconnecting portions of the container. Such interconnecting portions may be folded portions which are adapted to be unfolded into the expanded state and/or one or more bellows portions comprised in the container. For instance, the container may comprise a first layer and a second layer which at one side are joined by an interconnecting bottom wall portion (which may suitably be of the same material as at least one of said first and second layers, or from a different material). The opening of the container would be on the opposite side relative to the bottom wall portion. The bottom wall portion may be joined to the first and second layers by any appropriate seam, such as a weld seam. In an unused state, the bottom wall portion may, at the seams be folded over one of said first and second layer so that the container is in a collapsed state. When waste is to be placed in the container, the bottom wall portion is unfolded, whereby the container is expanded to present a large internal volume. Thus, the function is similar to foldable shopping bags having a rigid bottom portion. It should be understood that the expansion may be accomplished with other types of foldable portions and seams in order to accommodate for large items in the container. For instance, instead of or in addition to an interconnecting bottom wall portion, the first and second layers of the container may be spaced apart by one or more interconnecting side portions.

From the above, it should be understood that, according to at least one exemplary embodiment, said at least one sterilized wound care article comprises at least one absorbent wound pad.

According to a second aspect of the inventive concept, a method of using a wound care product in accordance with the first aspect is provided. The method comprises:

opening said sterilized sealed chamber to provide access to said sterilized wound care article, removing said container from said sterilized wound care article, opening said container to provide access to said interior container space, optionally, separating from said removed wound care article part or parts which will not be used for treating a wound at issue, placing a used wound care article and/or said optionally separated part(s) in said interior container space, reclosing said container for closing said interior container space, and applying said sterilized wound care article on the wound.

It should be understood that the method is not limited to performing the steps in the above presented order. A different order is conceivable. Furthermore, other steps may be included as well. For instance, placing a used wound care article in said interior container space may be preceded by a step of removing that used wound care article from the wound. The step of applying said sterilized wound care article on the wound may be performed before the step of reclosing said container; the step of opening said container may be performed after the step of removing a used wound care article from the wound; etc. Furthermore, the method may comprise even further steps, for instance, removing a release layer/liner from the sterilized wound care article. Such a release layer/liner may be regarded as one of said parts which will not be used for treating the wound and is separated from the new wound care article. Other such parts may be bits of foam and filler material, or packaging material not forming part of the container etc, as has been previously exemplified in this disclosure.

BRIEF DESCRIPTION OF THE DRAWINGS

FIG. 2 illustrates the use of a container comprised in a wound care product according to at least one exemplary embodiment, for instance, the one illustrated in FIGS. 1a-1b.

FIG. 3 illustrates the use of another container comprised in a wound care product according to at least some exemplary embodiments of the inventive concept.

FIGS. 5a-5b illustrate a wound care product according to at least a further exemplary embodiment of the inventive concept.

DETAILED DESCRIPTION OF THE DRAWINGS

Figure 1A:
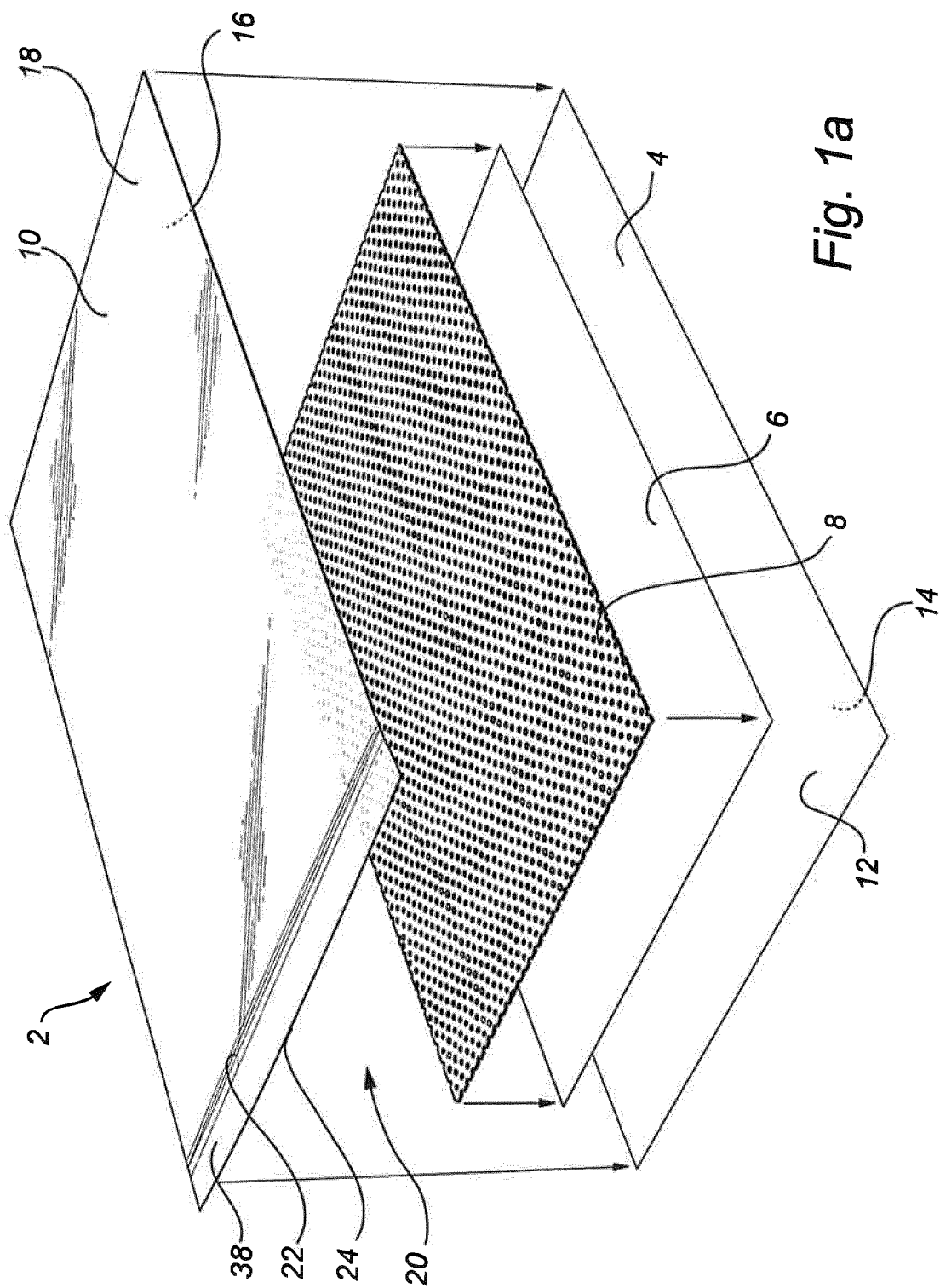
FIGS. 1a-1b illustrate a wound care product according to at least one exemplary embodiment of the inventive concept.
Figure 1B:
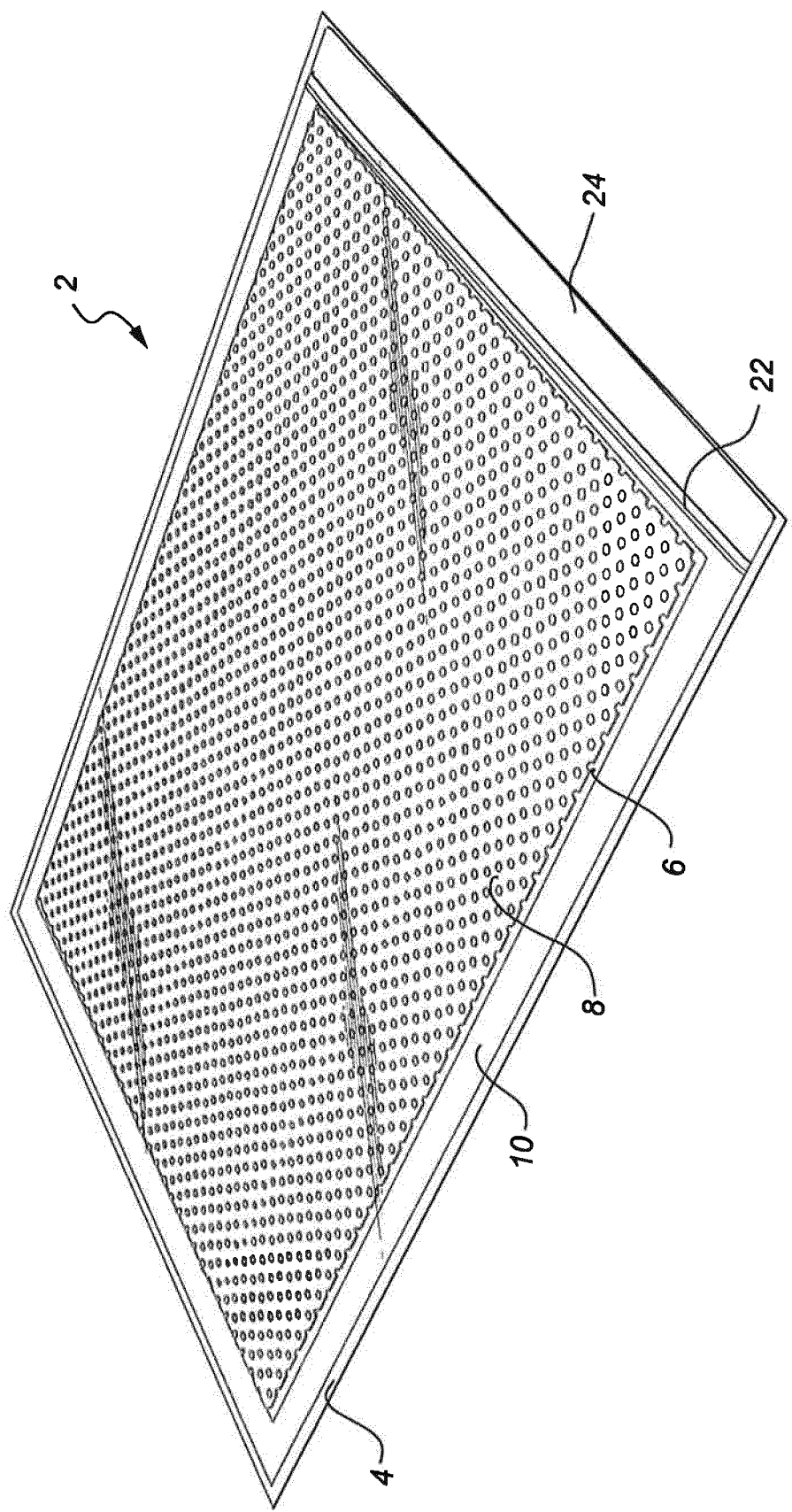

FIGS. 1a-1b illustrate a wound care product 2 according to at least one exemplary embodiment of the inventive concept, of which FIG. 1a is an exploded view of at least some of the components that may be included, and FIG. 1b is a perspective view of the assembled wound care product 2, which would normally be an unused state of the product.

Referring to FIG. 1a, the illustrated wound care product 2 comprises four components. Starting from the lowermost component to uppermost component as illustrated in the drawing, there is provided a front layer 4, a release layer 6, a wound care article 8 and a container 10.

The front layer 4 has an inside surface 12 and an outside surface 14. The inside surface 12 is facing the other components 6, 8, 10, while the outside surface 14 faces away from the other components 6, 8, 10. The outside surface 14 may suitably present a printed product description and other information. The front layer 4 may be made of a paper and may suitably be, permeable to a sterilizing agent, typically a sterilizing gas, such as Ethylene Oxide. However, other sterilizing methods for embodiments of the present inventive concept are also conceivable. Sterilization can be achieved by any one or a combination of known protocols in the art, some of which are standardized and approved by regulatory bodies. Non-limiting examples of sterilization methods for wound care products include autoclaving, exposure to dry heat, exposure to ultraviolet radiation, ethylene oxide treatment, gamma irradiation, immersion in aqueous alcohol solutions (e.g., 70% or greater concentrations of ethanol), gas plasma technology, steam sterilization, and electron beam irradiation. The choice of sterilization method can be influenced by a factor such as the type of material, which may have varying abilities to withstand and/or retain desirable characteristics under different sterilization protocols. For example, some ethylene oxide treatment protocols are well suited for sterilization of polymer foam materials.

The wound care article 8 is herein illustrated as a wound contact layer to be applied to a wound. An example of a conceivable wound contact layer is marketed by Mölnlycke Health Care under the trademark Mepitel®. At least one of the sides of the wound care article 8 is coated with an adhesive (not shown). In this illustration, the wound care article 8 is coated with an adhesive on the side facing the front layer 4, however, in other embodiments it could be on the side facing the container 10. The release layer 6 is attached to the adhesive coating to prevent the wound care article 8 from sticking to the front layer 4 or inadvertently getting adhered prematurely to other items. Thus, the release layer 6 is suitably removed just before applying the wound care article 8 onto the wound.

The container 10 is herein illustrated as a plastic transparent bag, however, as previously explained, other material types and configurations are also conceivable. The container 10 has outer surface portions 16, 18, of which one side 16 faces the other components 4, 6, 8 and the other side 18 faces away from the other components 4, 6, 8. Thus, the component facing side 16 of the outer surface portions, is in this exemplary embodiment sealingly attached to the front layer 4 to form a sealed chamber 20. After sterilization, for instance, as described above, the sealed chamber 20 will define a sterile environment. Thus, it should be understood that at least part (side 16) of said outer surface portions will be in said sterile environment.

As seen in FIG. 1b, when the wound care product 2 is provided in its unused state, a complete package for the wound care article 8 is formed by the front layer 4 and the container 10. The latter one will thus have the function of a back layer. This complete package may be an inner package which in turn could be provided in an outer package, such as a carton containing a plurality of such wound care products.

Thus, according to at least some exemplary embodiments of the inventive concept, the wound care product is in the form of a package having a front layer and a back layer, enclosing a wound care article, wherein the back layer is formed by an openable and reclosable container.

From the above, it should be understood that the container has a protecting function of the wound care article, before use of the wound care article. However, the container 10 has a dual functionality, since it may subsequently be used for receiving waste, such as used wound care articles removed from a wound, thus protecting staff, patients etc. from being unnecessarily exposed to contaminants from the waste. Apart from used wound care articles removed from the wound, the container 10 may also/instead be used for receiving waste material from the newly applied wound care article(s), e.g. release liners and unused bits of dressings. To this effect, the container 10 is openable and reclosable by means of an opening/closing means 22, herein illustrated as mutually cooperating zipper means, however, as previously explained other solutions are also conceivable. The opening/closing means 22 is located near an edge portion of the container 24. By opening the opening/closing means 22, access is provided to an interior container space 26 defined by inner surface portions 28 of the container (see FIG. 2). Waste, such as a used wound care article 30, may be disposed in the interior container space 26, as illustrated in FIG. 2. The container 10 may then be reclosed to reduce the risk of spreading any contaminants from said waste.

Although FIGS. 1a-b illustrate a wound care product with four components, it should be understood that more or fewer components would be conceivable. For instance, another release layer could be present if the wound care article is coated with an adhesive on the other side as well, in which case the number of components would be five. Conversely, a wound care article could be provided without a release layer, in which case the number of components could be reduced to three. For instance, an adhesive coating of the wound care article could be attached to the container, which would thus have release liner functionality. Of course, some wound contact articles, such as wound pads wound gauzes or cleansing fabrics, could be provided without an adhesive coating.

Although each one of the components has been illustrated as rectangular, having two long edges and two short edges, it should be understood that other embodiments with other shapes are also conceivable. Some non-limiting examples are square shaped, curved, oval, circular, or even irregular shapes, for instance adapted to different types of wounds at different body portions. Furthermore, the components may have mutually different shapes. For instance, the front layer and the container may have one shape, such as a substantially planar rectangle, while the wound care article may have another shape, such as provided with rounded corners.

In use of the wound care product, a method having the following steps may be performed:

The sterilized sealed chamber 20 is opened by, at least partly, separating the container 10 from the front layer 4. The sterilized wound care article 8 can then be accessed and removed. The container 10 is opened and waste, such as a used wound care article 30 to be replaced, is placed inside the container 10, i.e. in the interior container space 26. The container 10 is then reclosed and may be disposed of. In the example of FIGS. 1a-1b, the release layer 6 is removed from the wound care article 8, before it is applied to the wound to replace the used wound care article 30.

As can be seen from FIGS. 1a-1b, the container 10 is substantially flat before use. As seen in FIG. 2, the container may comprise a first layer 32 and a second layer 34 attached to said first layer 32 to define said interior container space 26. The second layer 34 extends beyond an edge 36 of the first layer 32 to form a grippable tab 38. The tab 38 facilitates the separation of the container 10 from the front layer 4 to enable access to the sterilized wound care article 8 in the sealed chamber 20 formed by the container 10 and the front layer 4. Thus, the tab 38, or at least a peripheral area thereof, is not adhered to the front layer 4. Suitably, the first layer 32 of the container 10 forms the seal with the front layer 4.

The first 32 and second 34 layers are connected to each other along edge portions 40, 42, 44. In FIG. 2, this is illustrated as connections at three out of four peripheral edges (at two long edges 40, 44 and one short edge 42 opposite to the opening at the opening/closing means 22). The volume of the interior container space 26 is increased from its flat unused condition, when the opening/closing means 22 is opened and waste is placed in the container 10.

FIG. 3 illustrates another exemplary embodiment of a container 50, the interior container space 52 of which may be increased to an even larger volume compared to the interior container space 26 in FIG. 2. As such, the larger volume, may receive greater amount of waste 54 or more bulky type of waste, such as the kits 92, 112 illustrated in FIGS. 5a-5b and FIG. 6, respectively. In FIG. 3, the first 56 and second 58 layers of the container 50 are connected to each other via an interconnecting bottom wall portion 60, allowing a greater expansion of the container 50 than the direct edge to edge connection shown in FIG. 2.

Figure 4:
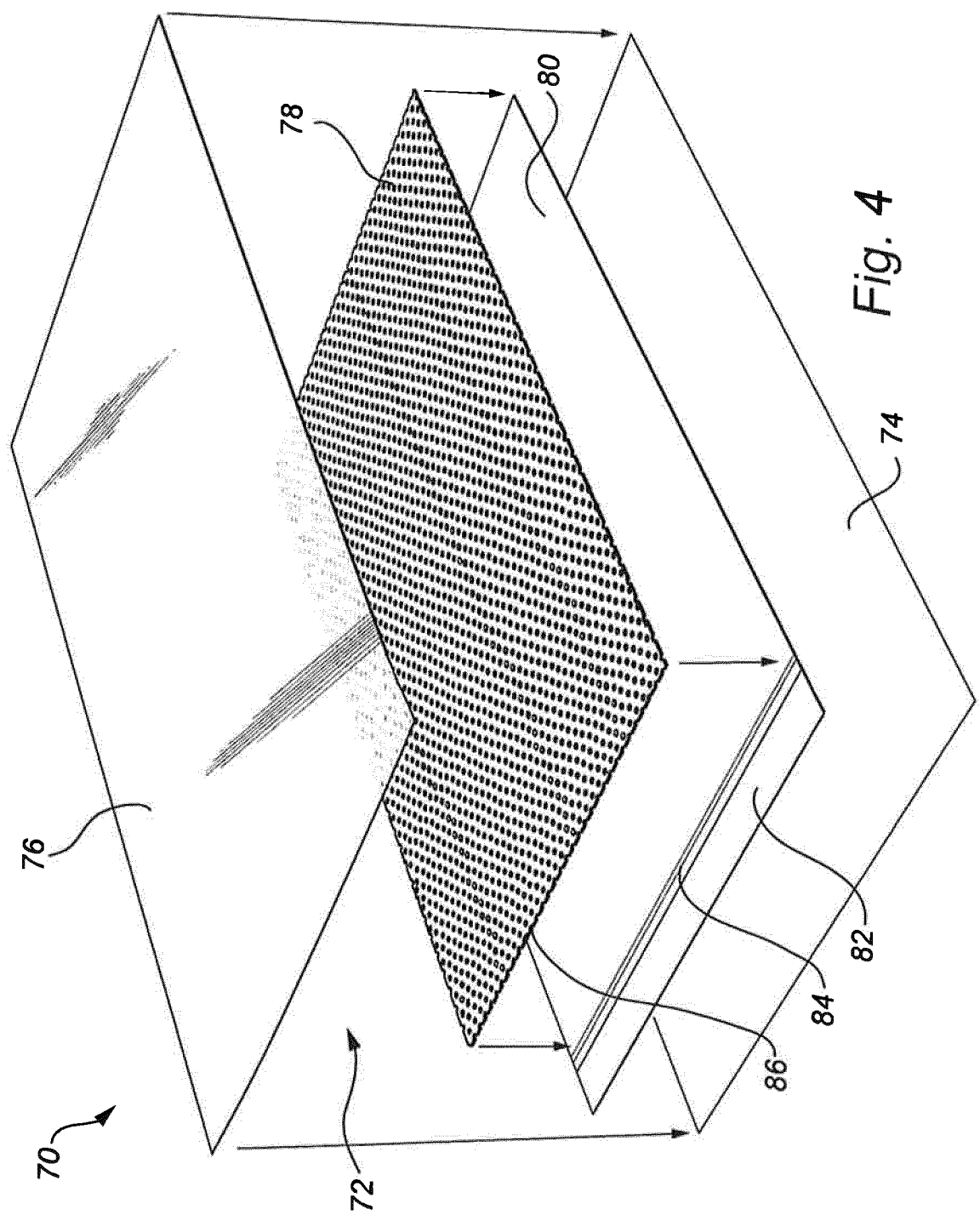
FIG. 4 is an exploded view of components included in a wound care product according to at least one exemplary embodiment of the inventive concept.

FIG. 4 is an exploded view of components included in a wound care product 70 according to at least one exemplary embodiment of the inventive concept. In this exemplary embodiment, the sterilized sealed chamber 72 will be formed by a front layer 74 to which a back layer 76 has been sealingly attached along the peripheral edge areas of the front 74 and back 76 layers. The back layer 76 may be transparent. The sterilized sealed chamber 72 houses a wound care article 78 and a container 80. The wound care article 78 may be either coated with an adhesive or may be provided without an adhesive coating. In case of an adhesive coating being present, the container 80 may be attached to the adhesive coating and act as a release layer. A grippable tab 82, which may be formed by, at least one of a first and a second layer of the container 80, can be used for gripping the container 80 and peeling it off the wound care article 78 before it is applied to wound. The tab 82 extends from the opening/closing means 84 of the container 80, and may extend beyond a peripheral edge 86 of the wound care article 78, which is suitably located on the other side of the opening/closing means 84 compared to the tab 82.

Although all container embodiments have been illustrated with a grippable tab being delineated by, and along, the opening/closing means, it should be understood that other solutions are also conceivable. For instance, the grippable tab does not need to extend along the entire length of the opening/closing means; it could be formed by a smaller tongue, as long as it allows separation from the wound care article or front layer (depending on which of the shown embodiments it is implemented on).

If the wound care article 78 in FIG. 4 lacks an adhesive coating, the container 80 could either be located on one side of the wound care article 78 acting as an additional protecting layer, or the unused wound care article 78 could even be located inside the container 80 (provided that the container is not closed or of a material permeable to a sterilizing agent). Thus, it should be understood that in all the embodiments, an outer surface portion of the container will be in the sterilized environment of the sterilized sealed chamber, and the container will have an initial protecting function before the wound care product is opened and used, and will then have a "waste bag" function for taking care of used products and/or other waste.

Figure 5A:
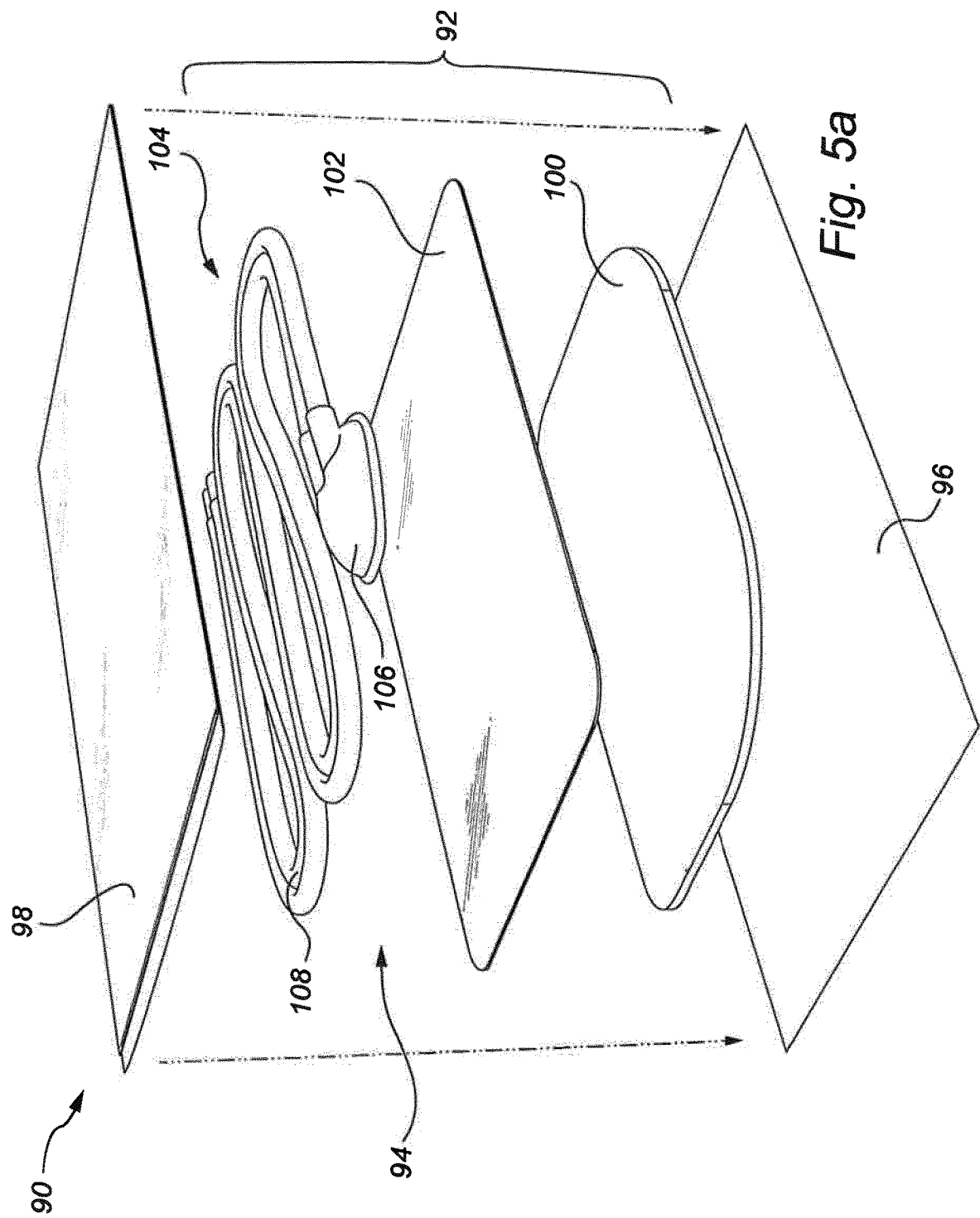

FIGS. 5a-5b illustrate a wound care product 90 according to at least a further exemplary embodiment of the inventive concept. FIG. 5a is an exploded view and FIG. 5b is a perspective view of the assembled wound care product 90. In this exemplary embodiment, several wound care articles are included in the form of a negative pressure wound therapy (NPWT) kit 92 arranged in a sterile environment of a sealed chamber 94 formed by a front layer 96 and a container 98.

The kit 92 includes a large wound pad 100 to be placed in the wound, a wound cover 102, and a conduit 104 configured to transmit negative pressure from a negative pressure source. The conduit 104 is illustrated as having a cup- or bowl-shaped nozzle 106 and a multi-lumen tube 108. Although the container 98 is illustrated in the same way as in FIGS. 1a-1b and FIG. 2, another alternative would be to have a container with larger interior space volume, such as the one illustrated in FIG. 3. Other container configurations for receiving used bulky items such as the tubing and large pad, or simply more waste, may include containers having various types of folded portions and/or one or more bellows portions.

Figure 6:
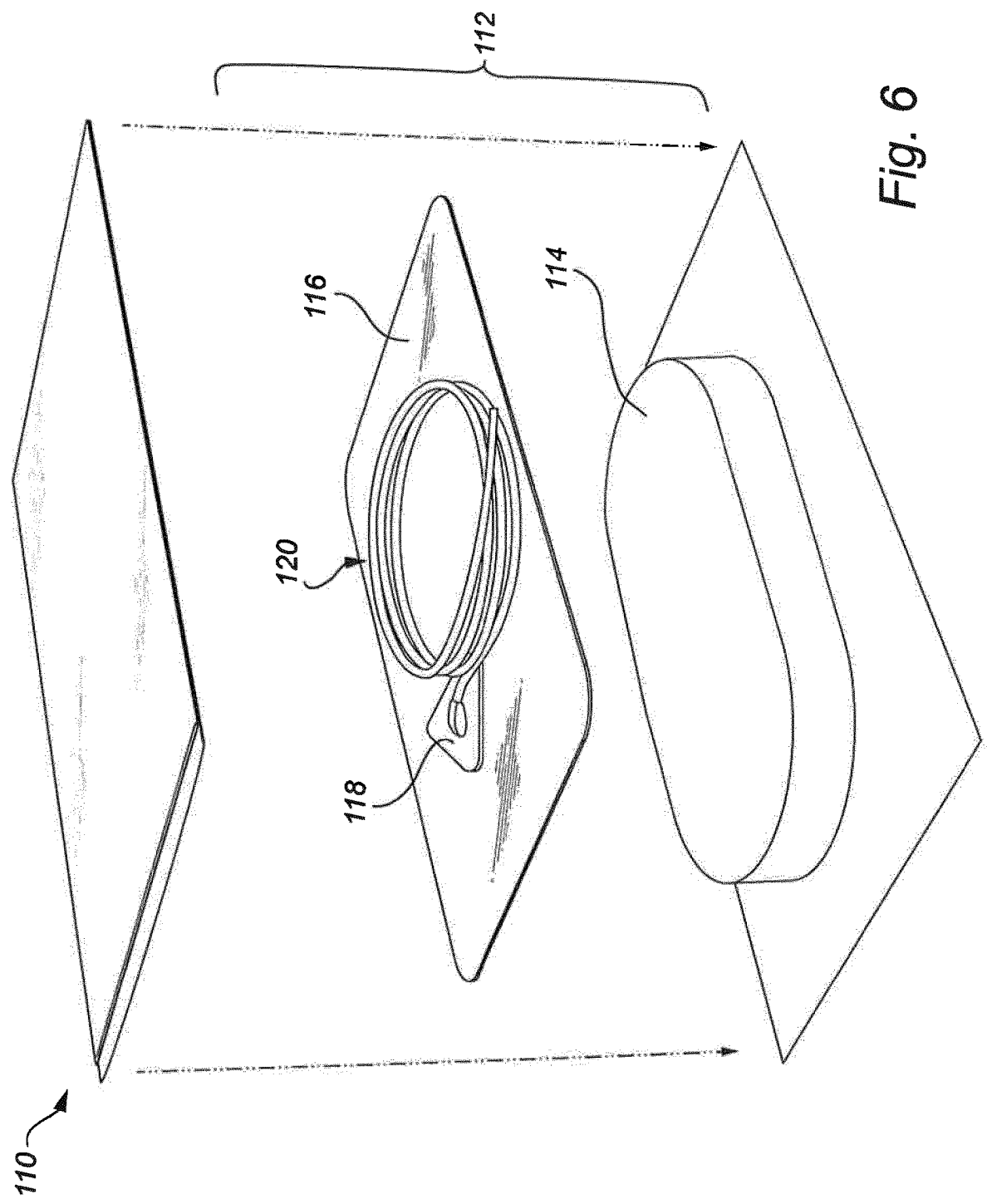
FIG. 6 is an exploded view of components included in a wound care product according to at least another exemplary embodiment of the inventive concept.

FIG. 6 is an exploded view of components included in a wound care product 110 according to at least another exemplary embodiment of the inventive concept. This exemplary embodiment is similar to the one illustrated in FIGS. 5a-5b, however, instead of a wound pad, FIG. 6 illustrates a foam dressing 114 as one of the components of a NPWT kit 112. The foam dressing 114 is illustrated as having a substantially oval form, but may be provided in other shapes as well. Furthermore, the surgical personnel may cut and shape the foam dressing 114 so that it conforms to the wound in which it is to be applied. The kit 112 also comprises an adhesive film 116 which is then placed over the applied foam dressing 114 and the wound, and a small hole may be cut through the film 116 above the foam dressing 114. The nozzle 118 of the conduit 120 is attached to the film 116 above the hole and the conduit 120 is connected to a negative pressure source for commencing a negative pressure wound therapy. The Avance® NPWT system marketed by Mölnlycke Health Care comprises such a kit which could be packaged in a wound care product according to the inventive concept.

Although different exemplary embodiments have been illustrated, it should be understood that these are merely non-limiting examples. Furthermore, it should be understood that the dual functionality of the container is not limited to the above examples. In particular, it is to be noted, that a container which is included in a wound care product together with one type of wound care article, is neither limited to nor necessarily intended to receive a corresponding used wound care article for disposal. For instance, a container may form part of a wound care product which also includes a bulky wound care article, such as a foam dressing. The container will thus have a protecting function for the unused foam dressing, but may subsequently be intended, or at least used, for receiving a less bulky used wound care article, such as a thin wound contact layer.

It should also be understood that the term waste material is not limited to material which has been used for treatment. It can be rejected material as well. For instance, as previously exemplified it may include unused bits of foam or filler.

Furthermore, the present inventive concept may be used with other wound care articles than those illustrated in the drawings. For instance, the container may be used for receiving swabs, wipes, or other materials getting in contact with a wound. It may be used for receiving wound diagnostic devices, such as a point of care device.

The invention claimed is:

1. A wound care product, comprising
 a sterilized sealed chamber defining a sterile environment,
 at least one sterilized wound care article contained in the sterilized sealed chamber,
 a container having inner surface portions defining an interior container space and outer surface portions facing away from said interior container space, the container being openable for enabling access to said interior container space while maintaining said sterile environment of said sterilized sealed chamber and reclosable for closing said interior container space, wherein at least one of said outer surface portions is in said sterile environment.

2. The wound care product as claimed in claim 1, wherein said sterilized sealed chamber is at least partly defined by a gas permeable front layer.

3. The wound care product as claimed in claim 2, wherein said sterilized sealed chamber is at least partly defined by said container, said container being releasably attached to said front layer.

4. The wound care product as claimed in claim 3, wherein one of the outer surface portions of the container faces said front layer and is at its periphery or near its periphery sealed to said front layer.

5. The wound care product as claimed in claim 2, wherein said sterilized sealed chamber is at least partly defined by said outer surface of said container, said container being releasably attached to said front layer.

6. The wound care product as claimed in claim 1, wherein said sterilized sealed chamber is at least partly defined by a back layer, said back layer being releasably attached to said front layer.

7. The wound care product as claimed in claim 1, wherein said container is releasably attached to said at least one sterilized wound care article.

8. The wound care product as claimed in claim 7, wherein said sterilized wound care article comprises a wound contact layer provided with an adhesive coating, wherein one of the outer surface portions of the container forms a release layer releasably attached to the adhesive coating on the wound contact layer.

9. The wound care product as claimed in claim 1, wherein said container is in the form of a bag.

10. The wound care product as claimed in claim 1, wherein said container comprises:
 a first layer, and
 a second layer attached to said first layer to define said interior container space, wherein the second layer extends beyond an edge of the first layer to form a grippable tab.

11. The wound care product as claimed in claim 10, wherein said first layer is sealingly and removably attached to said front layer to form said sterilized sealed chamber.

12. The wound care product as claimed in claim 10, wherein said first and second layer comprises mutually cooperating zipper means for opening and closing the container.

13. The wound care product as claimed in claim 12, wherein said grippable tab extends from said mutually cooperating zipper means to an edge of said second layer.

14. The wound care product as claimed in claim 10, wherein the container is expandable such that in an expanded state said first layer and said second layer are, at least locally, spaced apart by an interconnecting portion of the container.

15. The wound care product as claimed in claim 1, wherein said at least one sterilized wound care article comprises at least one absorbent wound pad.

16. The wound care product as claimed in claim 1, wherein said sterilized sealed chamber is at least partly defined by a layer which does not form part of the container.

17. A method of using a wound care product as claimed in claim 1, comprising,
 opening said sterilized sealed chamber to provide access to said sterilized wound care article,
 removing said container from said sterilized wound care article, opening said container to provide access to said interior container space,
 optionally, separating from said removed wound care article part or parts which will not be used for treating a wound at issue,
 placing a used wound care article and/or said optionally separated part or parts in said interior container space,
 reclosing said container for closing said interior container space, and applying said sterilized wound care article on the wound.

* * * * *